US00PP12229P2

(12) United States Plant Patent
Lemon

(10) Patent No.: US PP12,229 P2
(45) Date of Patent: Nov. 27, 2001

(54) VARIETY OF GERANIUM PLANT NAMED 'PATRIOT BRIGHT RED'

(75) Inventor: David Lemon, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/715,317

(22) Filed: Nov. 17, 2000

(51) Int. Cl.[7] ..... A01H 5/00

(52) U.S. Cl. ..... Plt./330

(58) Field of Search ..... Plt./330, 325

*Primary Examiner*—Amy J. Nelson
*Assistant Examiner*—Kent L. Bell
(74) *Attorney, Agent, or Firm*—Webb Ziesenheim Logsdon Orkin & Hanson, P.C.

(57) ABSTRACT

A new and distinct zonal geranium plant with bright red colored flowers above medium green foliage with distinct zonation.

1 Drawing Sheet

BACKGROUND OF THE INVENTION

The present invention comprises a new and distinct cultivar of *Pelargonium×hortorum* known by the varietal name 'Patriot Bright Red' (Oglevee No. 5309, Breeder No. 4DG1569). The new variety was discovered in a selected breeding program in Lompoc, Calif. The new variety is a selection from the cross of (U.S. Plant Pat. No. 8,053) 'Sassy Dark Red', the female parent, and 'Avenida', the male parent (unpatented). The new variety was first asexually reproduced by cuttings at Oglevee, Ltd. Connellsville, Pa. The new variety has been trial and field tested at Connellsville and has been found to retain its distinctive characteristics and remain true to type through successive propagations.

The cultivar, when grown in a glass greenhouse in Connellsville, Pa. using natural light and temperatures of 60° F. night and 68° F. day, has a response time of six weeks from a rooted cutting to flowering in a 10 cm pot. The response time was determined on plants grown in soilless media employing constant fertilizer 200–250 parts per million of nitrogen and potassium in full light. Plants of 'Patriot Bright Red' differ from the plants of the parental cultivars primarily in flower color.

DESCRIPTION OF THE DRAWINGS

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions carried out in Connellsville, Pa. The color readings were taken indoors under 200–220 foot candles of fluorescent cool white light. Color references are primarily to The R.H.S. Colour Chart of The Royal Horticultural Society of London. Plants described were about 6 weeks old from a rooted cutting.

PLANT

Classification:
- *Botanical.*—*Pelargonium×hortorum.*
- *Commercial.*—Zonal geranium.

Form: Medium mound.
Height: 14.0–17.0 cm from soil to top of foliage.
Growth: Upright, free basal branching.
Strength: Does not require artificial support.
Foliage: Prominent zonation; stalked leaf attachment.
Rooting time: Roots visible in 14–21 days.
Leaves:
- *Size.*—Length: 6–7 cm. Width: 6.5–8 cm.
- *Shape.*—Reniform; cordate base.
- *Margin.*—Crenate.
- *Texture.*—Pubescent.
- *Color.*—Upper surface: Green Group 143A. Lower surface: Green Group 138B. Zonation: Green Group 137A.
- *Ribs and veins.*—Venation: Palmate. Color: Yellow-Green Group 145A.

Petioles:
- *Color.*—Yellow-Green Group 144A.
- *Length.*—5–6 cm.

Stem:
- *Color.*—Yellow-Green Group 144A.
- *Internode length.*—2.5–4.5 cm.

THE BUD

Shape just prior to anthesis:
- *Overall.*—Elliptical cluster.
- *Individual bud.*—Elliptical.

Size when just showing color:
- *Overall.*—4.5 cm across.
- *Individual bud.*—1 cm long; 0.8 cm wide.

Number of buds per cluster: 24–30.

INFLORESCENCE

Blooming habit: Continuous; free and early flowering.
- *Size.*—10 cm across.
- *Borne.*—Flower on umbel; umbel on pedicel; pedicel on peduncle; 6.5–11 cm above foliage.

Flowers:
- *Form.*—Flat to slightly cupped; somewhat ruffled.
- *Number of flowers per umbel.*—21–25.
- *Size.*—Diameter: 6.5–8.0 cm.
- *Petals.*—Color: Upper Surface: Red Group 45B. Some petals shade to an area of Red Group 44B and Red Group 43C toward the center of the petal. Base of petal is white. Some petals have veining of Red Groups 46A and 46B. Lower surface: Red Group 43A, some Red Group 43C with veining showing through. Eye: None. Shape: Obovate. Size: Length: 2.2–2.7 cm. Width: 1.5–2.5 cm. Margin: Entire. Number per flower: 6–9.

Texture and appearance: Smooth, velvety, highly reflective.

Tonality from a distance: Clear bright red flowers, with older flowers taking on a deeper blue-red color above medium green foliage with a zone present.

Petaloids:

*Quantity.*—0–3.

*Shape.*—Irregular; some twisted; some holding pollen.

*Color.*—Same as petals.

Pedicel:

*Length.*—1.5–3 cm.

*Color.*—Red Group 46A at top near flower shading to Yellow-Green Group 144B at base.

Peduncle:

*Length.*—17–18 cm.

*Color.*—Greyed-Purple Group 187B with Yellow-Green Group 144A.

Disease/pest resistance: No susceptibility to diseases or pests has been noted to date.

Lasting quality: Depending on conditions; the individual flowers and umbels will last 7–14 days. Overall blooming habit is continuous throughout the growing season.

REPRODUCTIVE ORGANS

Stamens:

*Anthers.*—1–2 mm.

*Filaments.*—Length: 0.4–0.7 cm. Color: White with pink/red tips. Pollen: Golden brown.

Pistils:

*Number.*—One.

*Length.*—1–1.5 cm.

*Stigma.*—Number: One; five parted. Color: Red-Purple Group 59C.

*Style.*—Length: 4 mm. Color: Red-Purple Group 59C.

Ovaries:

*Completeness.*—Superior.

*Pubescence.*—Very pubescent.

*Length.*—5–6 mm.

*Width.*—2–3 mm.

*Color.*—Yellow-Green Group 147D.

Fruit: Non observed.

GENERAL CHARACTERISTICS

1. 'Patriot Bright Red' exhibits clear bright red flowers above medium green foliage with a zone present.

2. As bloom ages flowers take on a deeper blue-red color giving this variety a unique look.

3. Cutting production and rooting speed is similar to the current market variety 'Alex' (U.S. Plant Pat. No. 5,311), commonly referred to as 'Kim' in the market place.

4. Plant habit slightly larger than 'Alex' but is not overly vigorous.

5. This variety has been trialed both indoors and outdoors during the growing seasons of 1996, 1997, 1998, and 1999 and has performed well under all conditions.

I claim:

1. A new and distinct variety of geranium plant substantially as shown and described.

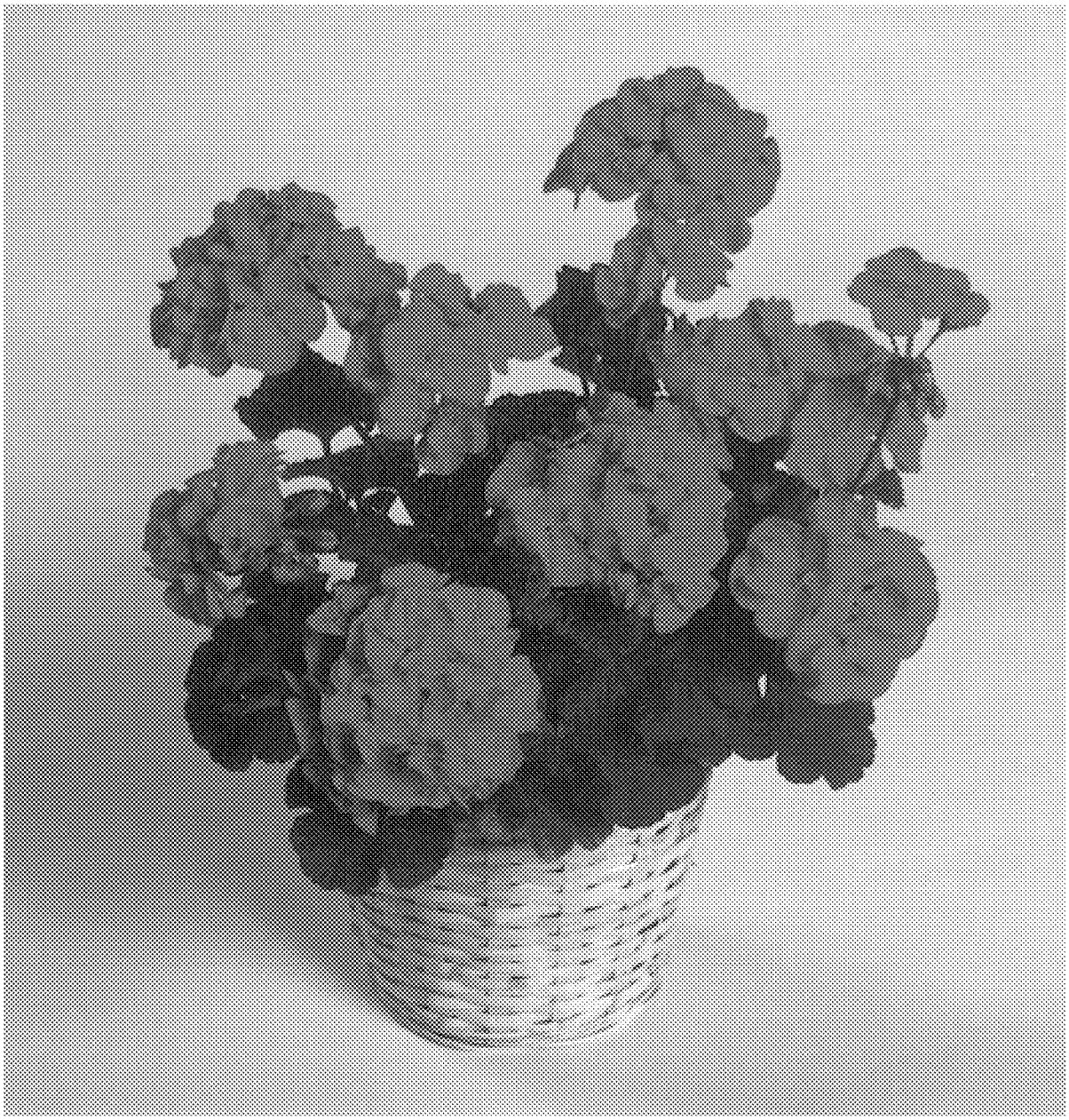

* * * * *